United States Patent [19]
Gough et al.

[11] Patent Number: 5,985,129
[45] Date of Patent: Nov. 16, 1999

[54] METHOD FOR INCREASING THE SERVICE LIFE OF AN IMPLANTABLE SENSOR

[75] Inventors: David A. Gough, Cardiff-by-the-Sea; Joseph Y. Lucisano, Sauqus, both of Calif.

[73] Assignee: The Regents of the University of California, Oakland, Calif.

[21] Appl. No.: 07/874,697

[22] Filed: Apr. 28, 1992

Related U.S. Application Data

[63] Continuation-in-part of application No. 07/450,852, Dec. 14, 1989, abandoned.

[51] Int. Cl.[6] .......................... C23F 13/00; G01N 27/26
[52] U.S. Cl. ................ 205/724; 128/903; 204/196.01; 204/400; 204/402; 204/403; 204/412; 204/415; 204/435; 205/775; 205/777.5; 205/778; 205/782; 205/782.5; 205/792; 600/347
[58] Field of Search ................................ 204/147, 148, 204/196, 197, 153.1, 153.12, 153.17, 400, 402, 403, 412, 415, 435, 196.1; 205/775, 777.5, 778, 782, 782.5, 792, 724

[56] References Cited

U.S. PATENT DOCUMENTS

| | | | |
|---|---|---|---|
| 2,508,523 | 5/1950 | Krebs | 204/198 |
| 2,563,062 | 8/1951 | Perley | 204/420 |
| 2,805,191 | 9/1957 | Hersch | 204/153.16 |
| 2,864,750 | 12/1958 | Hughes | 204/149 |
| 2,998,371 | 8/1961 | Sabins | 204/196 |
| 3,246,235 | 4/1966 | Allsopp | 324/29 |
| 3,249,250 | 5/1966 | Hermann | 204/15 |
| 3,300,345 | 1/1967 | Lyons | 136/86 |
| 3,308,046 | 3/1967 | Suleski | 204/196 |
| 3,458,421 | 7/1969 | Dahms | 214/402 |
| 3,505,195 | 4/1970 | Nielsen et al. | 204/435 |
| 3,616,412 | 10/1971 | Gnage | 204/195 |
| 4,036,716 | 7/1977 | Hulthe | 204/147 |
| 4,088,550 | 5/1978 | Malkin | 204/95 |
| 4,306,952 | 12/1981 | Jansen | 204/149 |
| 4,650,547 | 3/1987 | Gough | 204/1 T |
| 4,671,288 | 6/1987 | Gouth | 128/635 |
| 4,703,756 | 11/1987 | Gough et al. | 123/635 |
| 4,781,798 | 11/1988 | Gough | 204/1 T |
| 4,830,713 | 5/1989 | Gagescu | 204/402 |

OTHER PUBLICATIONS

Lucisano, et al., Anal. Chem., 59, 5, 736–739 (Mar. 1, 1987).
Lucisano, Ph.D. Dissertation, Univ. of Calif. (San Diego), pp xv–xvi, 8–10, 26–30, 34–36, 96–97 (made available to the public on Dec. 15, 1988)—Call No. "T3.6 .L82 1987".

*Primary Examiner*—T. Tung
*Attorney, Agent, or Firm*—Brown Martin Haller & McClain LLP

[57] ABSTRACT

Methods are described for extending the service life of implantable sensors having a silver-containing anodic reference electrode maintained at a high impedance, at least one noble metal cathodic working electrode, and at least one noble metal anodic counter electrode maintained at a low impedance, particularly sensors for the in vivo detection of oxygen and/or glucose in bodily fluids. The methods described involve increasing the input impedance of the reference electrode up to a maximum for implanted circuitry and shielding said electrode, and/or alternating the operating roles of the reference and working electrodes, switching the working electrodes with counter electrodes in the circuit, reversing the polarities of the reference and working electrodes, and sequentially activating each electrode in a plurality of working and/or reference electrodes in the circuit. All of the circuitry means needed to control the steps described can be implanted with the sensor so that the steps can be performed while the sensor is in use in a patient.

3 Claims, 3 Drawing Sheets

METHOD FOR INCREASING THE SERVICE LIFE OF AN IMPLANTABLE SENSOR

This application is a continuation-in-part of the U.S. application as Ser. No. 07/450,852, filed Dec. 14, 1989, now abandoned.

The Government has rights in this invention pursuant to Contract No. DK-27541-06 awarded by the National Institute of Health.

BACKGROUND OF THE INVENTION

1. Field of the Invention

The invention herein relates to implantable sensors for measuring bodily fluids. More particularly it relates to methods of extending the service life of such sensors.

2. Description of the Prior Art

The electrochemical oxygen sensor has been a powerful tool for revealing the role of oxygen in biological systems. Application of this sensor has been the main experimental methodology in many thousands of studies over more than 40 years. Virtually all, however, have been studies in which the sensor is used for a period of only a few days at most before recalibration is necessary. More recently there has been developed a stable oxygen sensor that is suitable for continuous application in long-term monitoring situations without the need of frequent recalibration. Such a sensor makes possible certain important oxygen monitoring applications that were not previously feasible.

This type of sensor, and its application as a component of an enzyme electrode-based system for continuously monitoring glucose, have been described in several prior patents: U.S. Pat. Nos. 4,650,547; 4,671,288; 4,703,756 and 4,781,798 the disclosures of which are incorporated herein by this reference. The system requires two oxygen sensors, one coupled to immobilized enzymes to detect oxygen modulated by the enzyme reaction, and the other to monitor the background oxygen concentration.

When a noble metal electrode (usually platinum or gold, which are slower to corrode than other metals) is immersed in an electrically conductive medium and held at a potential sufficiently cathodic with respect to an appropriate reference electrode, oxygen molecules in contact with the surface are reduced and an oxygen diffusion gradient is established, resulting in an electrical current. This phenomenon was observed and reported in the 19th century. Under controlled conditions, the reduction current may be related to oxygen concentration in the medium. This principle forms the basis of the amperometric (current-measuring) electrochemical oxygen sensor. It is recognized that the application of this principle will be influenced by factors such as: impurities in the media; pH and reaction intermediates; initial protonation of adsorbed oxygen; oxygen dissolved interstitially in the metallic electrode; the nature of the background electrolyte; and the degree of electrode surface oxide coverage.

The reaction pathways are complex. They include the kinetics of oxygen adsorption on and into the electrode and the formation of multiple metal-oxygen complexes involving short-lived intermediates. A detailed consideration of these pathways is not required here, but simplified models of the electrode reactions that are believed to explain many aspects are helpful in understanding the invention. These models are based on the observation that hydrogen peroxide is detected as an intermediate in the oxygen reduction process. One widely accepted mechanism in acidic media is the following two-step process:

$$O_2 + 2H^+ + 2e^- \rightarrow H_2O_2 \quad (1.1)$$
$$H_2O_2 + 2H^+ + 2e^- \rightarrow 2H_2O \quad (1.2)$$

In alkaline media, a similar process has been proposed:

$$O_2 + H_2O + 2e^- \rightarrow HO_2^- + OH^- \quad (2.1)$$
$$HO_2^- + H_2O + 2e^- \rightarrow 3OH^- \quad (2.2)$$

$HO_2^-$ is the ionized form of $H_2O_2$ that is present in alkaline media. These two sets of equations indicate that oxygen reduction can proceed by either a 2 or 4 electron process on platinum in aqueous solutions. These models have proven useful in analyses of functional electrodes.

When the electrode is polarized within a certain cathodic range, the rate of electrochemical reaction is sufficiently rapid that the process becomes mass transfer limited. This results in a current "plateau," in which there is relatively little variation in current with applied potential. The electrode can be most easily operated as a sensor in this potential range.

Certain three-electrode sensors of this type, especially those described in the aforesaid U.S. patents, have been shown to have long-term stability under well-defined in vitro and in vivo conditions. It has been found, however, that after a period of operation, such sensors tend to fail in one or the other of two characteristic modes. In most cases, the current rose abruptly and returned to the original value several times over the period of a few hours before finally remaining at a high, off-scale value. In other sensors, the current suddenly began to drift downward and fell over a period of several weeks.

It would be of significant value to have a method for preventing or deferring such failures, since such would be expected to substantially increase the operating service life of the sensors. It is therefore an object of this invention to provide such a method.

SUMMARY OF THE INVENTION

The invention herein is a method for extending the service life of implantable sensors containing silver or silver-containing electrodes, particularly sensors for the detection of oxygen and/or glucose in bodily fluids. Specifically, the invention is a method comprising, in a sensor having a silver-containing potential reference electrode maintained at a high impedance, at least one noble metal cathodic working electrode, and at least one noble metal anodic counter electrode maintained at a low impedance, operating both the reference electrode and the working electrode in the sensor with each in a first electrical state, and prior to occurrence of sensor failure, changing the electrical state of at least one of the reference electrode and the working electrode to a second electrical state and continuing operation of the sensor in that second state for a period of time extending beyond the time at which the sensor would have failed had the first electrical state in both electrodes been maintained.

In specific embodiments, the change in the electrical state of one or both of the working and reference electrodes may comprise: increasing the impedance at the reference electrode, preferably while shielding the electrode against effects of stray capacitance; electrically reversing the two electrodes; having a plurality of working and/or reference electrodes present, with only one of each active at any time, and sequentially replacing the operating electrode in the sensor circuitry with a second like electrode which was previously inactive; and/or periodically reversing the electrical potential to the working and the reference electrodes and maintaining that reversed state for an extended time.

DETAILED DESCRIPTION OF THE INVENTION

This invention is the result of discoveries made during the study of the failure mechanisms of the sensors described in the above-cited patents. It is therefore important to describe the normal operation of such sensors and the discoveries made about the failure modes, so that the method of this invention and its specific embodiments for extending the service life of such sensors will be fully understood.

Figure 1:
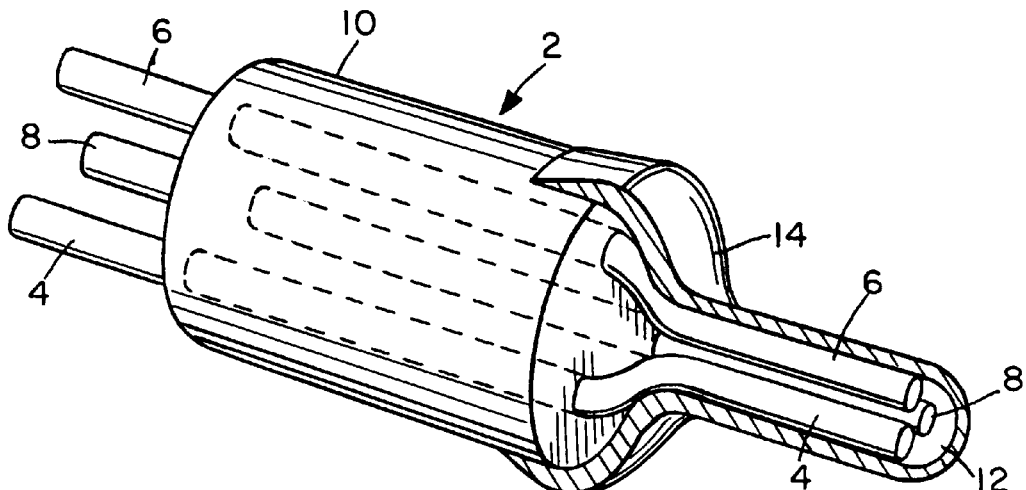
FIG. 1 is a perspective view, partially cut away, illustrating the basic sensor design applicable to this invention.

The basic sensor is illustrated in FIG. 1. The platinum working, silver/silver chloride reference, and platinum counter electrodes are fine wires embedded in an epoxy resin or glass cylinder and connected to more substantial lead wires not shown. The active electrodes extend from one end of the insulating cylinder and the lead wires extend from the opposite end. The electrodes are in electrolytic contact through an aqueous electrolyte gel and encased by an outer hydrophobic layer. The thin, cylindrical shape of the active region of this oxygen sensor readily allows for its inclusion in the two-dimensional glucose sensor described in the above-cited patents.

Test sensors were disassembled after a period of operation (commonly 120 days) for detailed microscopic examination. In a typical analysis, it was found that the reference electrode (originally formed from a solid silver wire, of constant 75 mm diameter) had partially dissolved, had become porous and had significantly corroded, with only approximately one half of its original material remaining at the time of examination. The degree of corrosion observed was approximately proportional to the time of operation of the sensor. Similar examinations of the working electrode showed that it had acquired a granular surface structure with use, which, according to X-ray elemental analysis, was a deposition of a thin layer of silver.

In the cases of gradual sensor failure (i.e., the gradual reduction of the electrical current generated by the electrodes), the original signal could be restored by appropriate polarization treatment or replatinization of the working electrode. In cases of abrupt sensor failure (i.e., a sudden and complete loss of current, a dendritic silver structure had formed a contact between the working and reference electrodes, apparently growing from the working electrode. In all cases, the counter electrode retained its original surface composition and microstructure and otherwise showed no change.

The microscopic examination indicates that various processes are believed to occur during operation. The working electrode gradually becomes coated with silver as a result of being cathodically polarized with respect to the silver source, the reference electrode. At that point, the oxygen-reduction process no longer occurs on a platinum surface. The deposition of silver apparently does not affect the signal as long as no dendritic contact with the other electrodes is made. The transfer of silver from the reference electrode was, however, somewhat surprising because the reference electrode is maintained at very high impedance by the potentiostat circuit ($>10^{-12}$ ohms based on the input impedance of the reference operational amplifier). Calculations show that a leakage current of $10^{-12}$ A between the two electrodes is sufficient in some cases to account for the small amount of material transferred. Transient local capacitive currents as a result of inadequate shielding of the lead wires may also have played a role. These currents, induced by external electromagnetic fields, were observed to reach peak values as high as $5\times10^{-9}$ A in other experiments involving electrodes placed in electrically "noisy" environments.

In most cases, sensor lifetime was limited by corrosion of the reference electrode, with failure occurring when a dendritic contact (formed from dissolved silver) ultimately connected the working and reference electrodes.

Based on these observations, the various embodiments of the method of this invention were developed. All rely on the basic principle of changing at least one of the working electrode and the reference electrode from the electrical and/or physical state in which it is originally operated to a second electrical and/or physical state, and then continuing the operation of the sensor with the electrode or electrodes operating in that second electrical state. It is believed that the prolongation of the service life of the sensors operated according to the method of this invention is due to the change in electrical and/or physical state reversing or slowing the transfer of metal from one electrode to the other and/or the formation of dendritic structures of metal between the electrodes.

One embodiment of the present method comprises increasing the input impedance at the reference electrode, preferably while shielding the electrode to counteract the effects of stray capacitance which would cause local currents. In this embodiment, one or more gain resistors and amplifiers are used to increase the input impedance at the reference electrode. It should be noted, however, that there is a practical limit to the increase in impedance possible in an implantable device, which limit is at the point where it would be necessary to thermally insulate the sensor, protection not available in an in vivo environment.

Figure 7:
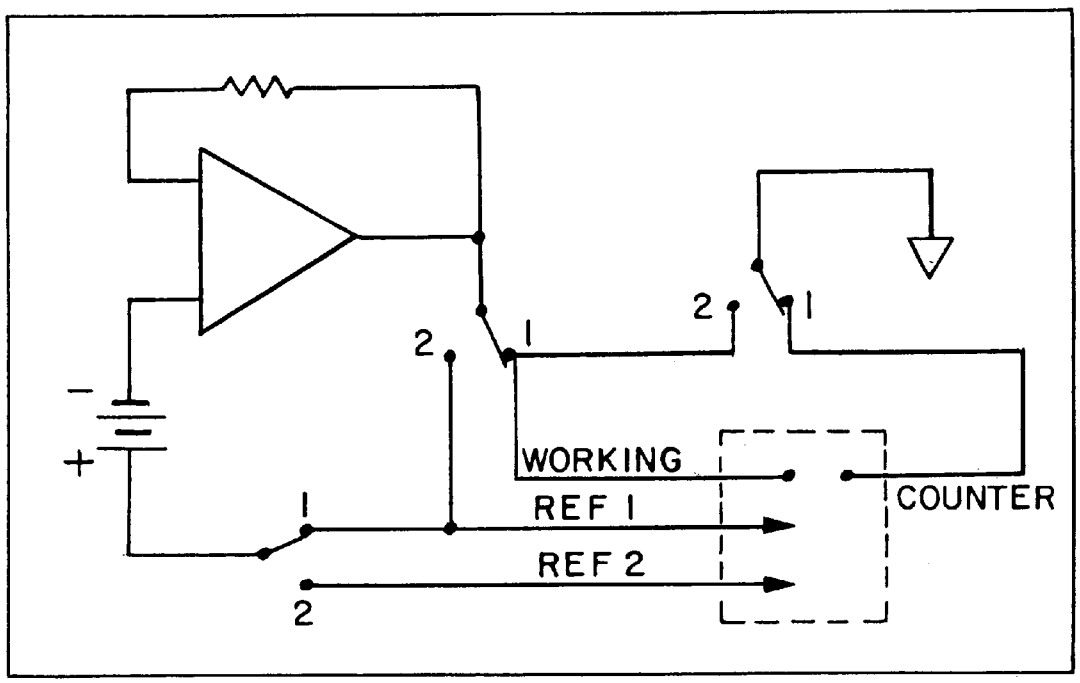
FIG. 7 is a schematic electrical diagram showing the circuitry of this invention in which the input impedance is increased.

An example of how a combination of resistors and amplifiers might be used to increase the input impedance in a potentiostat-circuit is shown in FIG. 7. In this example, the reference operational amplifier is maintained at an input impedance of at least $10^{12}$ ohms. When properly biased with respect to the reference electrode, the working electrode produces a cathodic current that is quantified as a voltage drop across the selected gain resistors $R_f$, $R_1$, and $R_2$.

Also, in operation the reference electrode is shielded according to means well known in the art, such as encompassing all or a part of the electrode in a conductive, noncorrosive metal layer such as copper or stainless steel wire. Although shielding in prior art sensors (particularly of working electrodes as in Perley, U.S. Pat. No. 2,563,062)has been taught to reduce stray capacitance and electrical noise in the protected lead to enhance the accuracy of measurements made with the electrode, these shielding methods are also useful to extend the life of the electrode when used in combination with the other steps of the methods of this invention. More specifics regarding shielding means effective in different applications, including a sensitive, high impedance circuit such as that used in this embodiment, can be found in Rich, *Analog Dialogue,* Vol. 17, No. 1, pp. 124–129 (1983), and in *Advancement of Medical Instrumentation Standard for ECG Connectors,* ECGC-5/83.

It should be noted that a certain degree of shielding and high impedance is intrinsic in a potentiostat circuit, yet neither these instrinsic levels nor shielding or increased impedance alone are sufficient to prevent sensor failure. Maximizing input impedance and improving shielding will assist in avoiding sensor failure but, as indicated above, this strategy is of limited usefulness in an implantable sensor. Therefore, additional or alternative strategies as described below are preferred.

Figure 3:
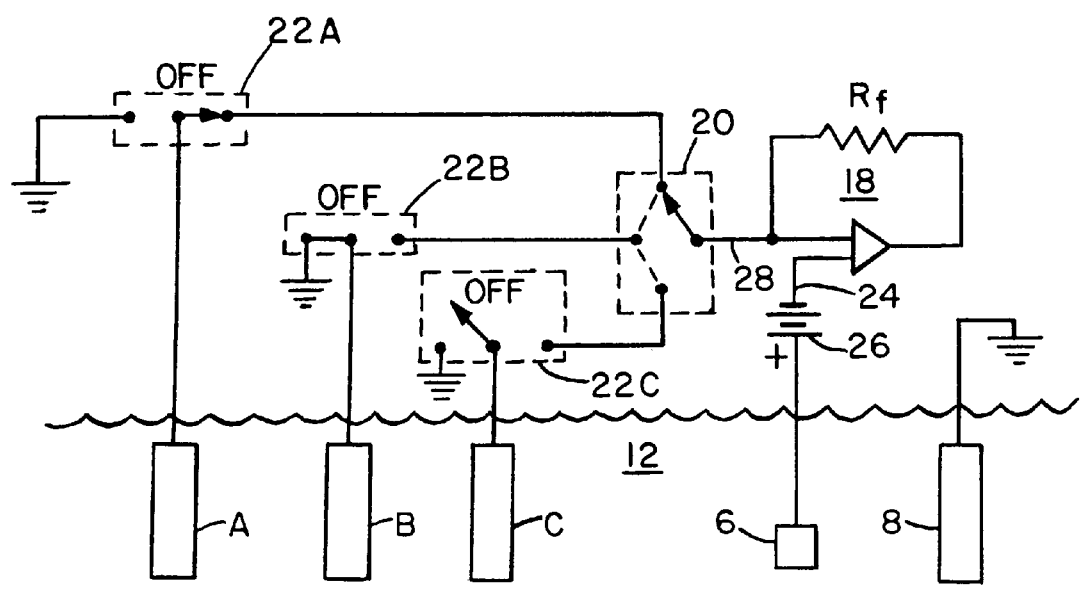
FIG. 3 is an schematic electrical diagram showing the circuitry of an embodiment of this invention in which a plurality of working and/or reference electrodes is used.

A second embodiment comprises, prior to formation of any dendritic structure bridging the two electrodes, reversing the electrical connections to the working and counter electrodes, as shown in FIG. 3, so that each assumes the prior operating role of the other. This will cause the new counter electrode to become cleaned of its accumulated layer of deposited silver and silver to become deposited on the new working electrode. This reversal can be repeated as long as the reference electrode remains functional and contains a sufficient amount of silver. This would require a relatively large reference electrode.

Figure 4:
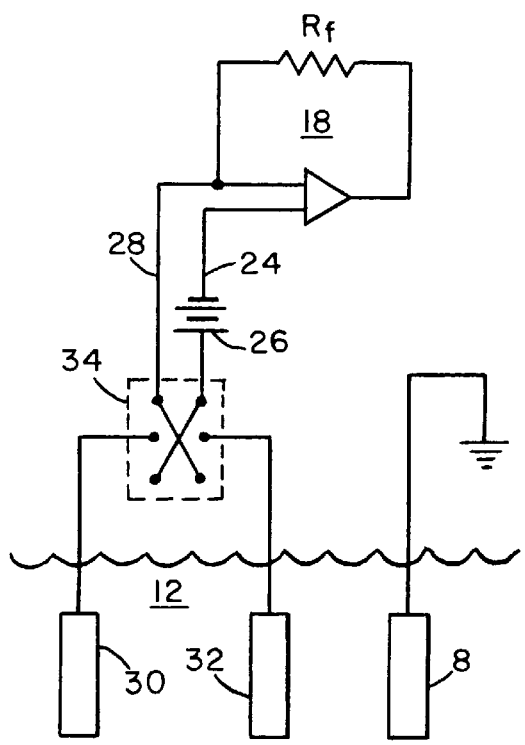
FIG. 4 is an schematic electrical diagram showing the circuitry of an embodiment of this invention in which the polarities of the working and reference electrodes are reversible.

A third embodiment comprises including in the sensor structure a plurality of working and/or reference electrodes, as shown in FIG. 4. Only one of each type of electrode would be operative as a working or reference electrode at any one time, and all electrodes of each type would be designed so that they could be connected sequentially into the sensor circuit. Thus as each working and/or reference electrode approached the limit of its service life because of metal deposition or removal, a second previously unused electrode could be switched into its place. In a preferred version of this embodiment, the extra working electrodes are initially incorporated into the sensor circuitry as counter electrodes and each operates as such until such time as it is needed as a replacement working electrode. This will enable the reserve working electrodes to maintain a deposit-free surface until each is used as a replacement for a previous working electrode.

With respect to the reserve reference electrodes, these would be most effective if they were relatively large.

While a more specific embodiment is shown in FIG. 3 (described below), FIG. 7 depicts an exemplary circuit to illustrate this method which would allow one of multiple working electrodes to be sequentially selected for use by positioning the switch at positions "1" through "4". Although this circuitry could be controlled manually, the preferred embodiment would incorporate the circuit into the implantable sensor controlled and constructed as, for example, described in U.S. Pat. No. 4,703,756 and in Gough, et al., "A Telemetry-Instrumentation System for Chronically Implanted Glucose and Oxygen Sensors", IEEE Transactions on Biomedical Engineering, Vol. 35, No. 7, pp. 526–532 (1988).

Those skilled in the art will appreciate that modifications to the depicted circuit (such as use of additional switches or solid state devices to perform the switching functions without departing from the the inventive method.

The fourth embodiment of this present method comprises periodically reversing the electrodes' polarization so as to change its physical state and drive electrodeposited metal (usually silver) from working electrode back to the reference electrode. This can be accomplished by reversing the polarity of the circuit such that the silver reference electrode becomes cathodic and the working electrode becomes anodic for a period of time sufficient to pass the required number of coulombs of silver from the working electrode to the reference electrode.

Figure 5:
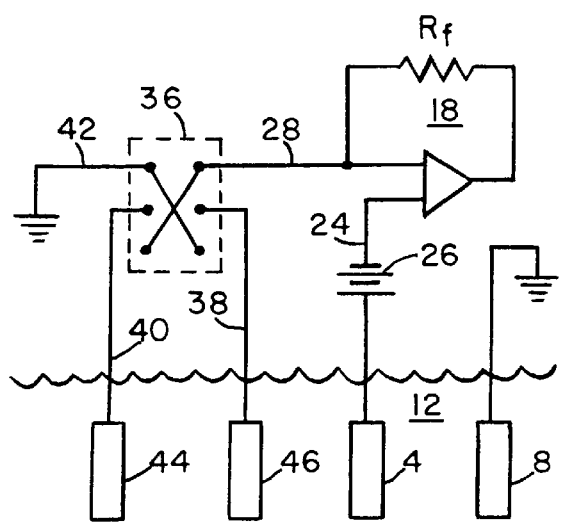
FIG. 5 is an schematic electrical diagram showing the circuitry of an embodiment of this invention in which the functions of the working and counter electrodes are reversible.
Figure 8:
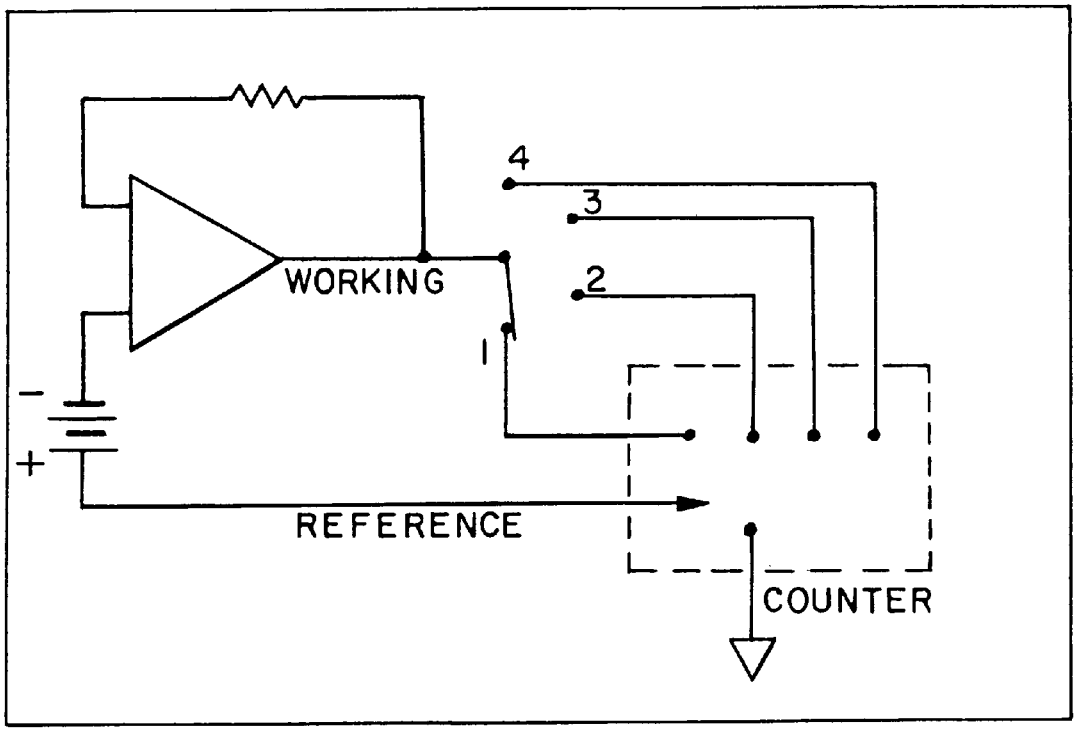
FIG. 8 is an exemplary schematic in which working and/or reference electrodes are sequentially switched into operation.

While more specific embodiments are shown in FIGS. 4–5 (described below) FIG. 8 depicts an exemplary circuit to illustrate this method which would allow the polarities of the circuit to be reversed. In this example, moving the switches from position "1" to position "2" places a negative potential on reference electrode number 1 (thus making it the "new" working electrode) and places a positive potential on the former working electrode (thus making it the "new" counter electrode). As a result, silver deposited on the original working electrode would deplete and become deposited on the original reference electrode. A second reference electrode (Ref. 2) is required to maintain operation in the switched configuration.

This circuitry can be implanted as described above with respect to the third embodiment of the invention. It will be appreciated by those skilled in the art that the circuit depicted in FIG. 8 could be modified (by, for example, allowing the sequential use of a series of reference and working electrodes as shown in FIG. 7 and periodically reversing polarities as shown in FIG. 8) without departing from the inventive method.

The fifth embodiment of this present method comprises employing means to pass a small, continuous cathodic current through the high impedance reference electrode. This current, while not large enough to cause significant polarization of the electrode, functions to prevent corrosion of the electrode material. It should be noted that the intermittent application of current will not be sufficient as it cannot be predicted when measurements obtained from the sensor could be affected by gradual or sudden sensor failure. To avoid loss or miscommunication of data from the sensor, therefore a continuous protective current must be applied.

It will be recognized that these embodiments may be used in various combinations with each other, and that such combinations may produce further extended services lifetimes. For example, a plurality of working and/or reference electrodes may be present and may be switched into the system, while at the same time the service life of each individual electrode may be extended by reversing the electrode's polarization periodically. This should result in a extension of the service life of each individual electrode and thus extend the time between the necessary replacements of electrodes from the plural supply of electrodes. Thus the cumulative effect of the combination of embodiments is a greatly extended service life for the sensor itself, and much longer intervals between implantations of fresh sensors.

Examination of the Figures of the drawings will further explain the embodiments of this invention. Referring first to FIG. 1, the basic sensor 2 used in the present method is illustrated. There are three electrodes, the reference electrode 4, the working electrode 6 and the counter electrode 8. The reference electrode 4 is a silver/silver chloride electrode while the working electrode 6 and counter electrode 8 are noble metal (preferably platinum) electrodes. A silver impregnated electrode; i.e., one which is composed of a matrix material such as silicone rubber, epoxide, or other hydrophobic or hydrophilic polymeric material in which particles of metallic silver are incorporated or dispersed to such a density that the particles are substantially in electrical contact, may also be used as the reference electrode. The three electrodes are formed of fine wire embedded in a glass or epoxy cylindrical housing 10 and are connected to more substantial lead wires (not shown). The electrodes are in electrical contract through an aqueous electrolyte gel 12. The electrodes 4, 6 and 8 are clustered outside of the housing 10 in a narrowed or necked region 14 which is covered by a hydrophobic oxygen permeable layer 16 of a material such as silicone rubber.

Figure 2:
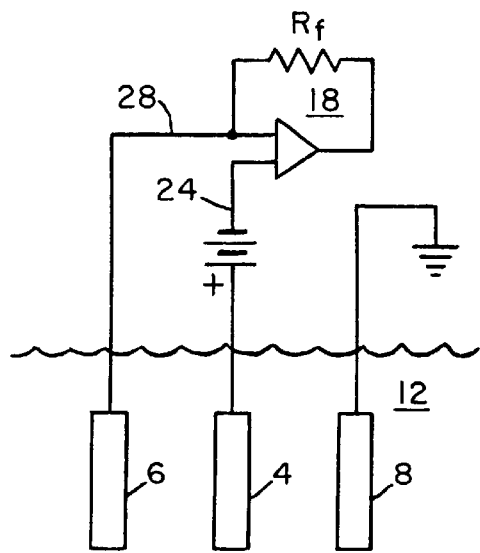
FIG. 2 is an schematic electrical diagram showing the basic circuitry of the sensors applicable to this invention.

The sensor 2 is operated on the classical potentiostatic principle which is illustrated schematically in FIG. 2. As with other types of sensors, oxygen is electrochemically reduced at the surface of the platinum working electrode 6, generating an electrode current that is proportional to the oxygen flux. The potential of the platinum working electrode is specified with respect to the silver/silver chloride reference electrode 4. In this mode of operation however, the reference electrode 4 is maintained electronically at a very high impedance to avoid significant current uptake. The main current passes to the inert counter electrode 8, which is maintained at low impedance. The operational amplifier circuitry 18 maintains the desired potential between the working and reference electrodes 6 and 4 by applying the appropriate potential between the working and counter electrodes 6 and 8. The voltage developed across the feedback resistor $R_f$ is proportional to the electrode current. This voltage is measured and processed by other circuitry not shown.

This three-electrode system provides separate electrodes for the two functions carried out by the anode in previous designs and has the advantage of directing very little current to the reference electrode 4. It makes possible the use of much larger ratios of the area of working electrode 6 to that of counter electrode 8, thereby producing larger currents. This makes signal amplification and noise reduction less critical in sensors of small overall size.

Embodiments of the method are illustrated graphically in FIGS. 3, 4 and 5. FIG. 3 shows an embodiment in which there are a plurality of working electrodes which can be switched sequentially into the system. Three electrodes (labeled A, B and C) comprise the working and reference electrodes. In the version shown in FIG. 3, electrode A is wired as the working electrode, electrode B is wired as an extra counter electrode (along with regular counter electrode 8) and electrode C is out of the circuitry. The selection of which electrode is the working electrode at any given time is by means of the combination of 3-pole, sequential throw switch 20 and the individual SPDT-center off switches 22 (respectively 22A, 22B and 22C in each path). As each working electrode becomes deteriorated or subject to coating or bridging, it is switched out of the circuit by opening its switch 22 (i.e., moving the switch to the center-off position as at 22C), moving the switch 20 to the next sequential position and closing that next electrode's switch 22 as shown at 22A. While the remaining fresh electrodes can be left out of the system (by having their switches 22 left open) if desired, it is preferred to have them temporarily wired into the circuit as additional counter electrodes as shown with electrode B and switch 22B to prevent them from becoming coated with metal deposits.

It will be apparent that FIG. 3 also illustrates the type of circuitry necessary for having a plurality of switchable reference electrodes. In this case the switch 20 would be placed in line 24 between the battery 26 and the plurality of electrodes. Each of the switches 22 could be SPST switches which would all be open except for the particular electrode which was then in use. One can also combine the presence of both extra working and reference electrodes by having separate switches 20 in each line 24 and 28 and sequencing the two parts of the circuit independently as needed.

While only three electrodes are shown in FIG. 3, it will be evident that there can be any number, limited only by the number of electrode wires which can conveniently be clusters in the sensor 2 in combination with the electrodes 4, 6 and 8.

FIG. 4 illustrates the embodiment where the polarity of the working and reference electrodes are reversible. In this case lines 24 and 28 lead into DPDT switch 34 which is wired such that throwing the switch reverses the leads to electrodes 30 and 32. Thus the electrodes 30 and 32 are connected alternatively as the working electrode in line 28 or the reference electrode in line 24.

FIG. 5 illustrates the embodiment where the functions of the working and counter electrodes are reversible. In this case lines 28 and 42 (the latter from ground 48) lead into DPDT switch 36 which is wired such that throwing the switch reverses the connections between lines 28 and 42 and the leads 38 and 40 from electrodes 44 and 46. Thus the electrodes 44 and 46 are connected alternatively as the working electrode in line 28 or the counter electrode grounded through line 42.

Figure 6:
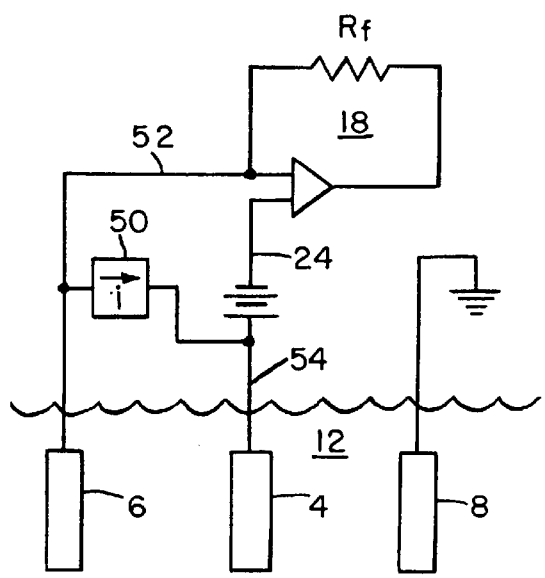
FIG. 6 is a schematic electrical diagram showing the circuitry of an embodiment of this invention in which a small cathodic current is caused to pass through the reference electrode.

FIG. 6 illustrates the embodiment where a controlled current source 50 is placed between the working electrode lead 52 and the reference electrode lead 54. This current source functions to pass a small, continuous cathodic current through the reference electrode 6. It will be recognized that the current source could be also placed in other areas of the circuit and achieve the same result.

The following examples will illustrate the sensors to which the service life extension method and embodiments of this invention can be applied. Electrodes were made by welding a small segment of 0.003 or 0.005-in.-diameter platinum or silver wire to one end of a long, PTFE-insulated stainless steel lead wire. The welded regions of two such platinum electrodes and one silver electrode were then encapsulated individually in the lumens of a short segment of multibore borosilicate glass tubing (0.010-in.-i.d., 0.062-in.-o.d.; Friedrich and Dimmock, Inc.) so that the electrodes and lead wires extended from opposite ends of the glass housing. A bisphenol A/epichlorohydrin-based epoxy resin (Stycast 1266, Emerson and Cuming, Inc.) was used for the encapsulation. Electrodes were carefully bent to the parallel arrangement shown in FIG. 1 and trimmed to a length of 0.02–0.10 in. The working and counter electrodes were platinized to a roughness factor of approximately 800, as estimated by anodic hydrogen stripping. The electrolyte gel was formed around the electrodes by dipping the end of the assembly in a 10–20% solution of poly(hydroxyethyl methacrylate) (Polysciences, Inc.) in methanol, allowing the solvent to evaporate, and hydrating with electrolyte. The electrolyte was 0.01 M phosphate buffer, pH 7.3, containing 0.01 M KCl. The gel filled in the spaces between the electrodes and provided a thin coating on the outer aspects. After drying, the outer hydrophobic layer was formed by dipping the end of the assembly in a solution of 25% silicone rubber (RTV 3140, Dow Corning Corp.) in toluene. The solvent was evaporated and the silicone rubber allowed to cure. This produced a layer approximately 10–25 um thick.

The gel could be dehydrated and rehydrated by exposure to an aqueous sample without loss of activity. The assembly was then fixed in a silicone rubber tube (0.040-in.-i.d., 0.085-in.-o.d., Dow Corning Corp.) in such a way that the lead wires were extended inside the tube and the active electrode region occupied one end. This recessed design presents an annular space around the electrodes which may be filled with an enzyme gel for enzyme electrode applications. The annular cavity was filled with silicone rubber (RTV 3140) or the tube was trimmed to expose the hydrophobic membrane-covered electrode assembly. The space surrounding the lead wires was filled with silicone rubber (RTV 615, General Electric Co.) to provide mechanical strength. A miniature electrical connector (Microtech, Inc.) was attached to the lead wires at their exit from the tube. This simple fabrication approach typically gave a high yield of sturdy, functional sensors.

Sensors were checked for uniformity prior to long-term testing. The integrity of the silicone rubber coating was determined by measuring the resistance with respect to an external electrode using a high impedance electrometer (Keithley Instruments Co., Model 616). Sensors with an apparent resistance of $10 \times 10^9$ ohms or greater could be used in complex media without interference from diffusible polar solutes and were considered to have an effective barrier. Sensors with significantly lower apparent resistance were recoated. The background current in the absence of oxygen was measured and determined to be insignificant. Linearity of the response over a physiologic oxygen concentration range was verified by exposing sensors to oxygen concentrations ranging from 0.02 to 0.24 mM, made by equilibrating buffer solutions with analyzed gas mixtures of 2, 5, 10 and 21% oxygen. Sensors typically required approximately one minute to return to steady-state after a step change in oxygen concentration.

Sensors were evaluated for stability in sealed, thermostated vessels at 37° C., containing 0.01 M phosphate buffer, pH 7.3. Solutions were maintained at desired oxygen concentrations by equilibration with analyzed gas mixtures. The concentration was changed at intervals of several days to demonstrate sensitivity. Electrode current was recorded continuously.

Six sensors were operated continuously in a sealed, thermostated vessel at 37° C., containing 0.01 M phosphate buffer, pH 7.3. The oxygen concentration was maintained at atmospheric levels by equilibration with filtered room air. Some sensors incorporated specific design modifications described below to determine their influence on reference electrode degradation. Sensors were otherwise identical to that shown in FIG. 1. Five sensors were disassembled after 70 days of continuous operation. One sensor was disassembled after 10 days of continuous operation. Reference electrodes were removed from the sensors and scanning electron microscopy was used to assess the extent of reference electrode degradation in each case. All reference electrodes were originally formed from solid, 75-mm-diameter silver wire.

A reference electrode was taken from a sensor that was subjected to the test conditions for 70 days but was not connected to any external circuitry to provide polarization of the working electrode. In this case, all electrodes were maintained at "open circuit" and were therefore not capable of sustaining DC current. This electrode served as a control in the experiment, since any corrosion in this case would be the result of simple electrolyte-silver interaction or passive noise pickup in the lead wires. Inspection by micrograph revealed little or no corrosion of this electrode.

Analysis by micrographs was made of reference electrodes taken from sensors that employed unshielded and shielded reference electrode lead wires, respectively. Both of these sensors were operated continuously for 70 days prior to disassembly. The reference electrode from the unshielded sensor exhibits substantially more corrosion than that from the shielded sensor. However, even the electrode in the shielded case showed significant corrosion over 20–30% of its surface. This indicates that lead wire shielding, although helpful in reducing corrosion, does not eliminate it under the conditions described here.

Also analyzed by micrograph was a reference electrode taken from a sensor that lacked an outer hydrophobic membrane.

This sensor was operated continuously for 70 days prior to disassembly. The electrode showed only minimal corrosion. The absence of the hydrophobic membrane in this case allows products from the anode and cathode reactions to diffuse out of the electrolyte gel surrounding the electrodes. This results in a lower steady-state concentration of those species at the surface of the reference electrode during sensor operation. The minimal degradation of this reference electrode suggests that the unidentified reaction products may be inherently corrosive to the electrode. Alternatively, the altered distribution of ionic current between the working and counter electrodes could be responsible for the decreased corrosion in this case.

Also analyzed by micrographs were reference electrodes taken from sensors operated continuously for 10 and 70 days respectively prior to disassembly. In these two cases, reference electrodes were subjected to a constant d.c. current instead of being maintained at high impedance. The current density in each case was $5.0 \times 10^{-7}$ A/cm$^2$. One reference electrode was subjected to an anodic current, while the other electrode was subjected to a cathodic current. The polarization induced in these electrodes by the forced current was measured and found to be less than 0.5 mV. These results dramatically demonstrate the effects of d.c. leakage currents on reference electrode corrosion. The sensor with impressed anodic current operated for only 10 days before failing due to dendritic contact between the reference and working electrodes. The corrosion rate of the reference electrode in this sensor was much greater than that of any other configuration. The sensor with impressed cathodic current, however, demonstrated a very low corrosion rate, as indicated by the lack of surface pitting. Some surface deposits (probably silver chloride) were noticeable on this specimen.

The observations described here suggest that the reference electrode in the unmodified sensor, although operating at very high impedance, was not truly reversible. This conclusion is consistent with previous experiments on bare and chlorided silver electrodes under similar conditions. Micropolarization studies with carefully prepared electrodes showed that the current is distinctly nonlinear and irreversible with small applied potentials (<1 mV) near the equilibrium potential, of the magnitude to which the electrode is exposed here. Under these conditions, the current may also exhibit very small transient drifts that cannot be attributed to the instrumentation. This suggests that increasing the input impedance and improving the shielding may not eliminate reference electrode corrosion.

The results of microscopic examinations have confirmed these predictions of reference electrode behavior. Shielding the electrode leads decreased reference electrode corrosion, but not to the extent required for very long-term operation. Further, operation without a hydrophobic membrane was seen to decrease corrosion, but this may be of little practical use when such a membrane is required to prevent electrode poisoning. The strongly corrosive nature of anodic leakage current was demonstrated. Finally, the strongly passivating (protecting) nature of impressed cathodic current was demonstrated. If this method is applied to increase sensor lifetime, then it is expected that other mechanisms of failure will become limiting factors. Degradation of the epoxy insulations, or corrosion of lead wires (some of which cannot be protected by imposed currents) may become important. Impressed cathodic current is often used to prevent corrosion in pipelines, bridges and other large structures (West, 1971), but has not been commonly applied to analytical electrode systems. The unique application proposed here, however, is expected to significantly extend sensor lifetime.

We claim:

1. A method for extending the service life of implantable sensors containing corrodible electrodes within a potentiostat sensor circuit having a sensor having a corrodible reference electrode, at least one noble metal cathodic working electrode, and at least one noble-metal anodic counter electrode maintained at a low impedance, which comprises applying to said reference electrode a continuous cathodic current.

2. A method according to claim 1 for extending the service life of implantable sensors containing corrodible electrodes within a potentiostat sensor circuit having a sensor having a corrodible reference electrode, at least one noble metal cathodic working electrode, and at least one noble metal anodic counter electrode maintained at a low impedance, which comprises increasing the input impedance at the reference electrode and shielding said reference electrode.

3. A method according to claim 1 wherein said corrodible electrode is a silver or silver-impregnated electrode.

* * * * *